United States Patent [19]
Mackool

[11] Patent Number: 5,730,156
[45] Date of Patent: Mar. 24, 1998

[54] METHOD FOR CUTTING AND REMOVING WRAPPING FROM AN INTRAOCULAR LENS IMPLANT WITHIN AN EYE

[76] Inventor: Richard J. Mackool, 31-27 41st St., Astoria, N.Y. 11103

[21] Appl. No.: 676,672

[22] Filed: Jul. 10, 1996

[51] Int. Cl.[6] .................................................... A61B 19/00
[52] U.S. Cl. ......................... 128/898; 606/107; 606/4; 606/6; 623/6; 604/22
[58] Field of Search ........................... 128/898; 606/107, 606/166, 169, 4–6; 604/22; 623/6; 206/5.1; 53/492, 50, 381.1, 381.2

[56] References Cited

U.S. PATENT DOCUMENTS

| | | |
|---|---|---|
| 4,228,341 | 10/1980 | Zandberg . |
| 4,538,608 | 9/1985 | L'Esperance, Jr. . |
| 4,836,201 | 6/1989 | Patton et al. ............... 606/107 |
| 4,869,715 | 9/1989 | Sherburne ................... 604/22 |
| 4,906,247 | 3/1990 | Fritch ........................ 623/6 |
| 5,026,393 | 6/1991 | Mackool . |
| 5,425,729 | 6/1995 | Ishida et al. ................ 606/13 |
| 5,505,693 | 4/1996 | Mackool . |

Primary Examiner—V. Millin
Assistant Examiner—Kelly O'Hara
Attorney, Agent, or Firm—Cobrin Gittes & Samuel

[57] ABSTRACT

A method of cutting and removing a wrapping from an intraocular lens implant within the eye. The method employs either a laser beam to effect the curing or an ultrasonic vibratory probe to effect the cutting. Once cut, the lens is free to unroll within the eye. The wrapping is then removed from the eye.

9 Claims, 5 Drawing Sheets

METHOD FOR CUTTING AND REMOVING WRAPPING FROM AN INTRAOCULAR LENS IMPLANT WITHIN AN EYE

CROSS-REFERENCE TO CITED PATENTS

U.S. Pat. No. 5,505,693, issued Apr. 9, 1996 to Richard J. Mackool, entitled METHOD AND APPARATUS FOR REDUCING FRICTION AND HEAT GENERATION BY AN ULTRASONIC DEVICE DURING SURGERY.

U.S. Pat. No. 5,026,393, issued Jun. 25, 1991 to Richard J. Mackool, entitled METHOD OF IMPLANTING AN INTRAOCULAR LENS IN A HUMAN EYE AND INTRAOCULAR LENS FOR SAME.

U.S. Pat. No. 4,538,608, issued Sep. 3, 1985 to L'Esperance, entitled METHOD AND APPARATUS FOR REMOVING CATARACTOUS LENS TISSUE BY LASER RADIATION.

U.S. Pat. No. 4,228,341, issued Oct. 14, 1980 to Zandberg, entitled MECHANICAL CONTROL SYSTEM PARTICULARLY USEFUL FOR DIRECTING A LASER BEAM.

BACKGROUND OF THE INVENTION

1. Field of the Invention

The present invention relates to a method of curing and removing wrapping from an intraocular lens implant within an eye.

2. Discussion of Related Art

The contents of U.S. Pat. No. 5,026,393 is incorporated herein by reference. This patent teaches a method of implanting an intraocular lens into a human eye.

This method calls for making first and second incisions of the eye, each incision being of a specified dimension and at specified locations. The first incision is arranged for insertion of the implant and removal of the wrapping and the second incision is arranged to allow an intraocular lens positioning tool to be inserted. A rolled intraocular lens having a wrapping about at least a portion of the lens is then pushed into the eye through the first incision. The wrapping is cut so that the lens unrolls in the eye. The cut wrapping is removed from the eye through the first incision while the position of the lens is maintained.

The intraocular lens, prior to insertion into the eye, is folded or rolled about its longitudinal axis together with the wrapping to maintain the lens in its compact, rolled configuration during insertion into the eye and to protect it from damage, such as from a tool. The wrapping may be positioned around the entirety or any part of the lens, such as around only the optical element or a portion thereof.

The wrapping is made of any suitable material, such as plastic, polypropylene, silicone, polyvinyl chloride or polytetrafluoroethylene, cellophane, or any other suitable pliable material. It preferably has a thickness in the range of 0.01 mm to 0.1 mm.

Removal of the wrapping is conventionally accomplished in many different ways, such as by mechanical or chemical means in accordance with the teaching of the '393 patent. Forceps can be used to peel or tear the wrapping during, or preferably after, lens insertion into the eye.

A small microsurgical instrument can be used to tear the wrapping, where the instrument includes an elongated shaft having an arcuate blade with a sharp cutting edge. The blade extends substantially perpendicular from the shaft and a hook is provided to grasp the wrapping and shield the lens from the blade.

Before using this small microsurgical instrument, the wrapping must be perforated so that the hook can be inserted into a perforated hole to initially grasp the wrapping prior to cutting with the blade. The wrapping is then cut with the blade along the perforation and standard forceps may be used to remove the cut wrapping from the eye through the incision. A positioning tool is inserted through the other incision and positioned to prevent movement of the lens and wrapping within the eye during removal of the small microsurgical instrument. Once the wrapping is cut by the small microsurgical instrument by tearing the wrapping along perforation, the lens unfolds.

Alternatively, a sharp knife can be used to start an incision in the wrapping and a hard firm rod or plate can be inserted along the length and inside of the wrapping to serve as a cutting board so that the lens is not damaged by the knife used to the cut the wrapping.

As another alternative, bonding of the wrapping to itself and/or to the lens may be chemically dissolved to free the lens to unfold. A dissociative chemisorption process may be used to effect this.

Also, the wrapping may be scored rather than perforated.

While the above techniques for removing the wrapping are satisfactory, other techniques may be more desirable.

SUMMARY OF THE INVENTION

One aspect of the invention relates to removing the sheath or wrapping from the rolled intraocular lens implant by first cutting the sheath or wrapping with laser radiation from a laser, such as one of the diode or YAG variety, and then allowing the lens to unroll within the eye. The laser radiation is applied to the sheath or wrapping either with a contact probe or with a non-contact laser delivery system.

Another aspect of the invention relates to removing the sheath or wrapping from the rolled intraocular lens implant by first incising the sheath or wrapping with an ultrasonic vibratory probe that vibrates in the same manner as the ultrasonic vibratory probes that are conventionally used for cutting tissue during cataract surgery.

BRIEF DESCRIPTION OF THE DRAWINGS

For a better understanding of the present invention, reference is made to the following description and accompanying drawings, while the scope of the invention is set forth in the appended claims.

DETAILED DESCRIPTION OF THE PREFERRED EMBODIMENT

The contents of U.S. Pat. No. 5,026,393 (the '393 patent) are incorporated herein by reference.

Figure 1:
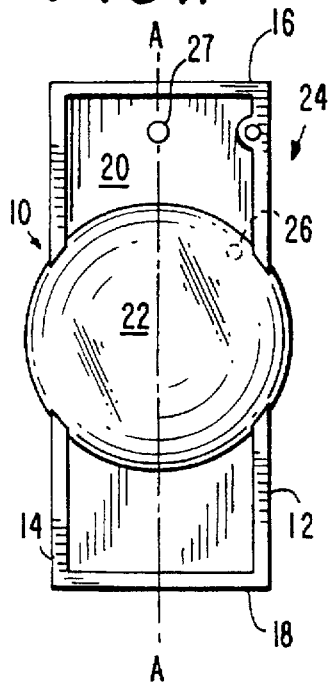
FIG. 1 is a top plan view of a conventional intraocular lens that can be used with the present invention.

Referring to the drawings in detail, and initially to FIG. 1 thereof, a conventional intraocular lens 10 includes two longitudinally extending opposed haptics positioning members by ribs 12 and 14 and ribs 16 and 18. A web of transparent material 20 extends between the ribs, except for the central portion of the intraocular lens where an optical element 22 is located and rigidly attached to ribs 12 and 14.

The entire lens is made of a soft material capable of being easily folded, such as hydroxyethylmethyacrylate (HEMA), silicone or other acrylic material. The soft material allows the lens to be folded and is optically acceptable. Thus, a small incision on the order of 2.0 to 3.5 mm or less is all that is required in accordance with the present invention for inserting the intraocular lens into its position within the eye. Older conventional techniques require incisions on the order of 3.5 to 4.5 min.

Intraocular lens 10 includes a pinhole 24 which is positioned in rib 12 adjacent rib 16. Pinhole 24 is of sufficient size so that the point of a positioning tool, to be later described, can be inserted therein to hold and/or position intraocular lens 10 in the eye. Alternatively, intraocular lens 10 can have a pinhole 26 positioned in optical element 22, or a pinhole 27 can be positioned in web 20. The pinhole may be surrounded by a second, more rigid material to prevent tearing of the softer silicone or other foldable material from the force exerted by the positioning tool engaged therein.

A first incision 28 is made in the eye at the junction of cornea 80 and sclera 82. The size of incision 28 will be determined by the dimension required for cataract removal and the dimension required for insertion of the implant. With modern equipment, cataract removal or excision by ultrasonic destruction and suction has been developed to a point whereby the cataract can be removed by an incision of 2.5 mm or less. However, heretofore, an incision of this size was insufficient to insert the intraocular lens implant and would have to be on the order of 3.5 to 4.5 mm.

Figure 2:
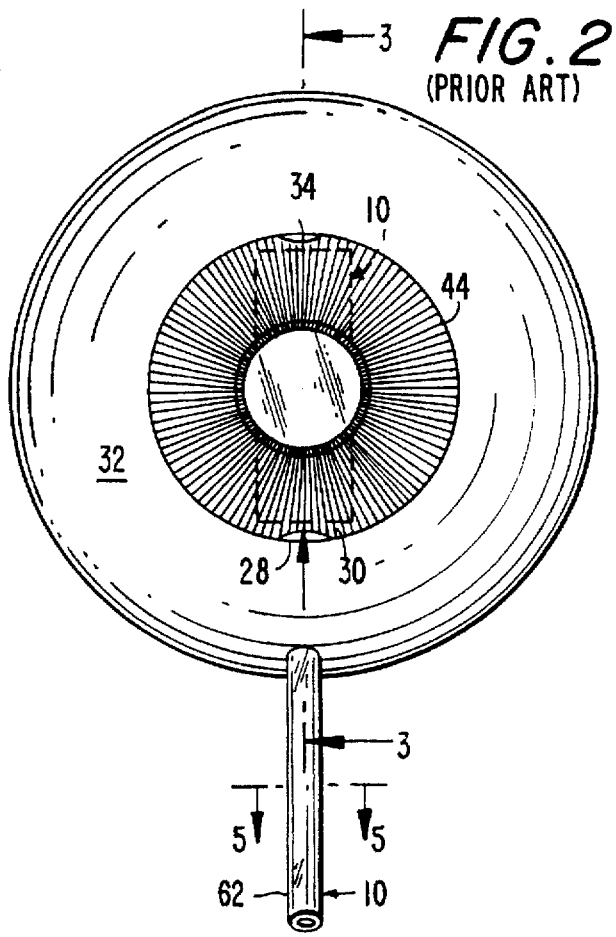
FIG. 2 is a front plan view of the intraocular lens of FIG. 1 rolled about its longitudinal axis together with a wrapping therearound and being inserted into the eye through an incision located between the cornea and the sclera.

According to the present invention, intraocular lens 10 is folded or rolled about its longitudinal axis A—A together with a wrapping 62, in much the same manner as rolling a newspaper. Thus, the rolled lens 10 and wrapping 62 can be inserted through incision 28 in the eye. Wrapping 62 is rolled with and around intraocular lens 10 to maintain intraocular lens 10 in its compact, rolled configuration, and to also protect intraocular lens 10 from damage from a tool or the like. Although wrapping 62 is shown in FIG. 2 as being wrapped about the entire length of lens 10, wrapping 62 may be pre-positioned around any part of lens 10, such as only the optical element 22 or a portion thereof. Further, lens 10 and wrapping 62 can be rolled together just prior to insertion thereof into the eye, or the same may be pre-rolled and pre-packaged. Also, the ends of wrapping 62 can be in abutting or overlapping relation.

Wrapping 62 may be made of any suitable material, such as plastic polypropylene, silicone, polyvinyl chloride, TEFLON (polytetrafluoroethylene), "Cellophane" or any other suitable pliable material, and preferably has a thickness in the range of 0.01 mm to 0.1 ram. In such case, rolled lens 10, together with wrapping 62, can be inserted through the 2.5 mm incision 28 in the eye. The thickness of wrapping 62 is sufficiently small so as not to hinder the insertion of lens 10 and wrapping 62 through incision 28.

Wrapping 62 may encase the rolled lens 10 and the tip of an instrument (not shown), such as a forceps, to be used for lens positioning or manipulation before or after unwrapping lens 10 in the eye.

Figure 8:
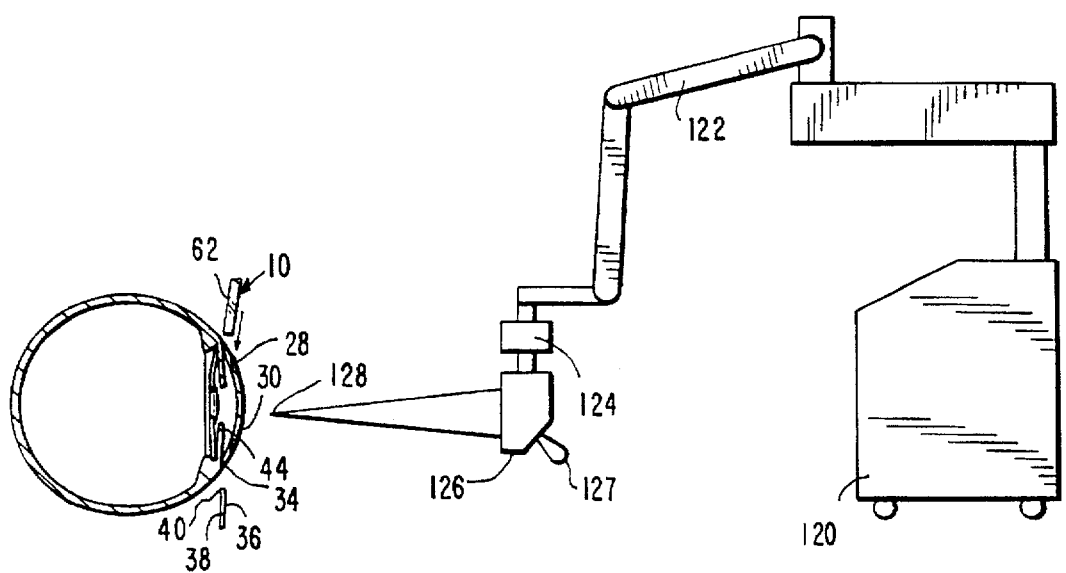
FIG. 8 is a schematic representation of a laser delivery system for free-hand surgery in accordance with the invention.

Prior to insertion of folded intraocular lens 10 and wrapping 62 through incision 28, a second puncture 34 is made in the eye at the juncture of the cornea and the sclera, opposite first incision 28. Puncture 34 is of the order of 1 mm or less, as such incision will accommodate the lateral dimension of a positioning tool which is inserted through puncture 84. The use of a puncture as described herein is standard operating procedure in cataract surgery and does not require a suture. One such positioning tool 36 is shown in FIG. 8 and includes an arm 38 having a pointed straight-hooked tip 40. The size of puncture 34 is sufficient to allow tip 40 and part of arm 88 to be inserted therethrough and 1 mm will usually suffice.

Accordingly, wrapping 62 and lens 10 can be inserted into the eye through incision 28 by a conventional tool.

Specifically, following cataract extraction through incision 28 by conventional means, intraocular lens 10 is folded about its longitudinal axis A—A, together with wrapping 62 therearound, such that pinhole 24 or 26 is exposed. A conventional forceps is used to insert the folded intraocular lens 10 and wrapping 62 into incision 28. The forceps is not inserted into the eye, thereby eliminating the need for a larger incision to accommodate this instrument and the potential for damaging intraocular structure with the instrument itself. Following lens insertion, positioning tool 36 is extended through puncture 34, and tip 40 grips pinhole 24 so that the folded intraocular lens 10 and wrapping 62 is held in its position while the wrapping 62 is removed. Because intraocular lens 10 is folded about its longitudinal axis, incision 28 is relatively small, on the order of 2.5 mm or less.

Figure 7:
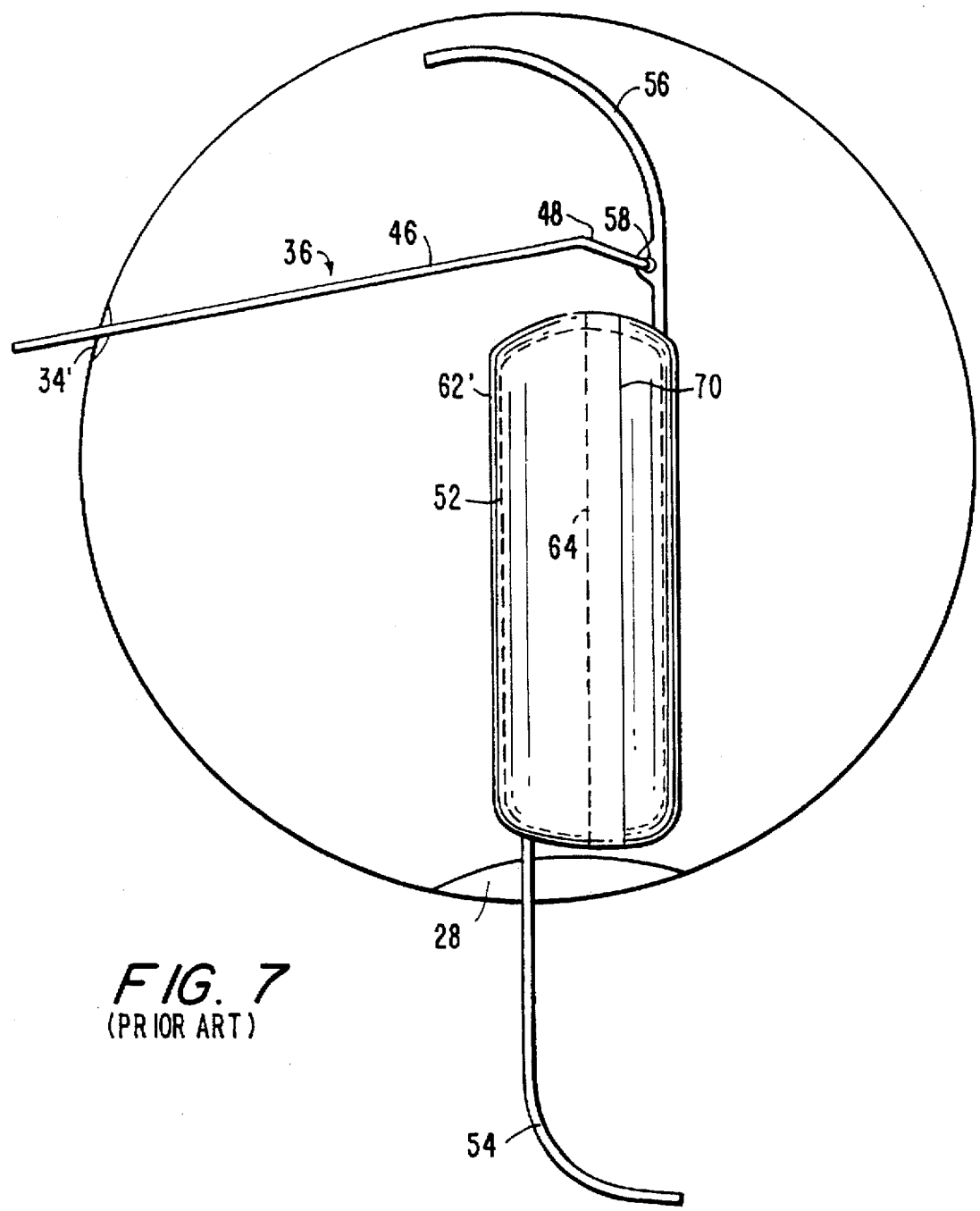
FIG. 7 is a front plan view of the intraocular lens and wrapping of FIG. 6 and inserted into the eye through an incision located between the cornea and the sclera.

Accordingly, lens 10 spontaneously unfolds, being kept away from contact with the cornea by a slight rearward (posterior) pressure by the surgeon upon the lens with the positioning tool so as to assume the position shown in FIG. 7.

After intraocular lens 10 is positioned as desired, which in most cases will be in the posterior chamber of the eye behind the iris 44, like the natural lens it replaces, the positioning tool 36 is removed through punctures 34. The net result is the implantation of the intraocular lens 10 in the posterior chamber of the eye with incisions on the order of 2.5 mm or less, which is less than those heretofore made.

Figure 4:
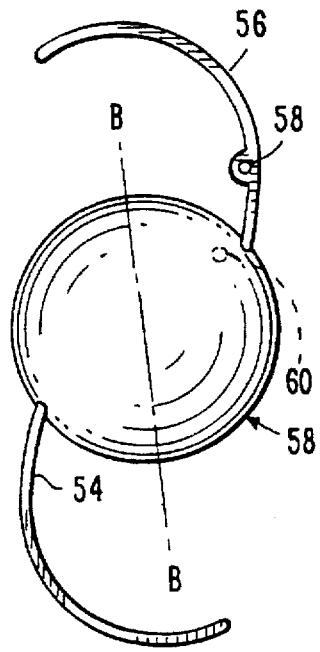
FIG. 4 is a top plan view of an alternative form of a conventional intraocular lens with haptics that can be used with the present invention.

In FIG. 4, an intraocular lens 50, which differs in design from intraocular lens 10 of FIG. 1, is shown. Intraocular lens 50 includes an optical element 52, made of silicone or other soft foldable lens material, having haptics positioning member 54 and 56 made of a non-soft standard material, such as PMMA or PROLENE (polypropylene). Positioning hole 58 can be formed at haptic 56 or, alternatively, at optical element 52, as shown in phantom lines by reference numeral 60. The positioning hole can be surrounded by a second, more rigid material, such as PMMA or other material, as described above.

The intraocular lens 50 is folded about its longitudinal axis B—B, together with a wrapping 62' such that pinhole 58 is on the exterior thereof. The insertion of intraocular lens 50 and wrapping 62' into the eye then follows the steps heretofore described in conjunction with intraocular lens 10.

Figures 5, 6:
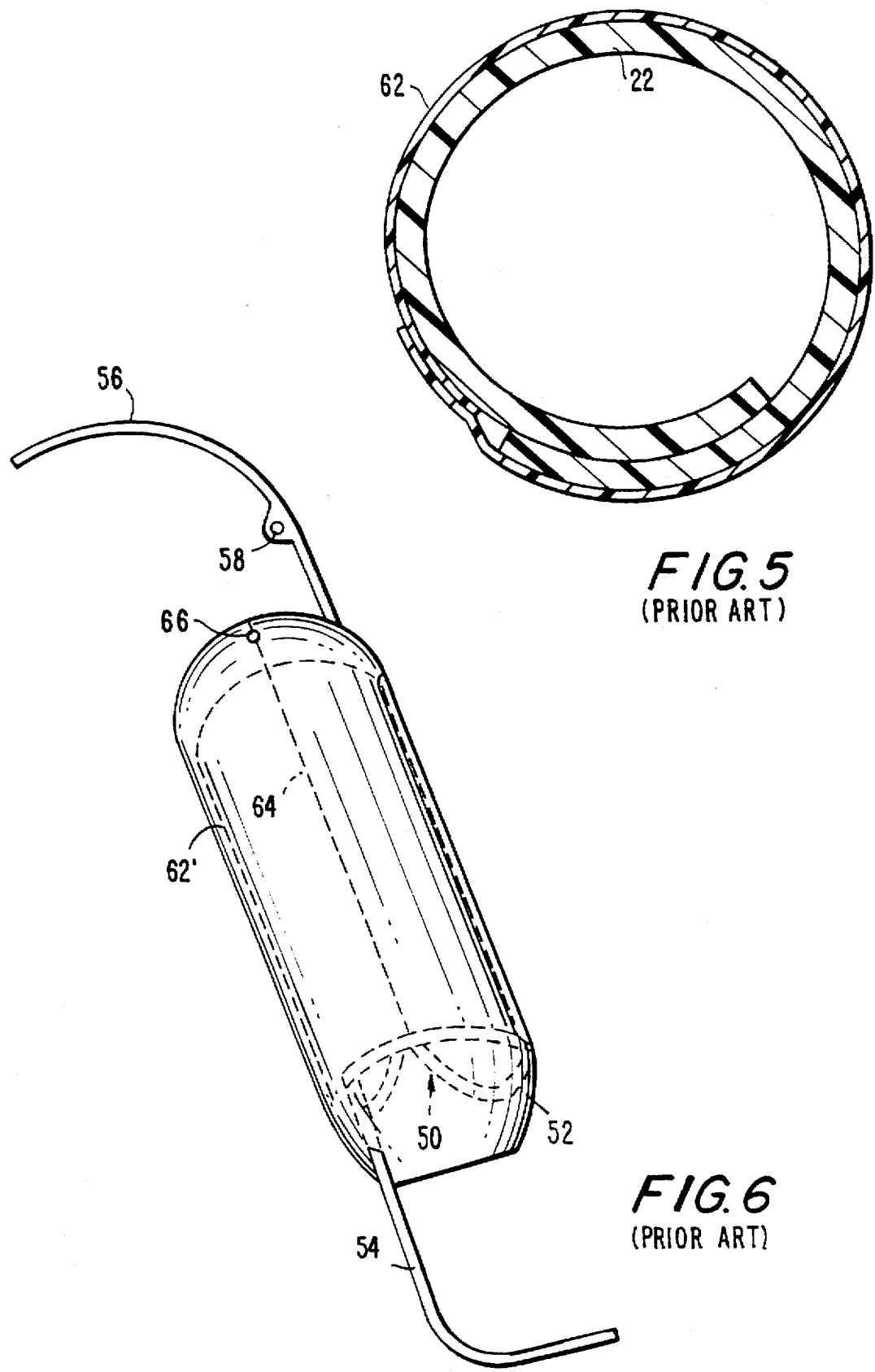
FIG. 5 is a cross-sectional view of the rolled lens and wrapping of FIG. 2, taken along line 5—5 thereof.
FIG. 6 is a perspective view of the lens of FIG. 4 rolled together with a wrapping for insertion in the eye.

Reference will be made to FIGS. 6 and 7, where wrapping 62' is formed with a longitudinal perforation 64 extending along the entire length thereof.

To prevent lens 50 and wrapping 62' from moving within the eye during removal of instrument 68, the microsurgical positioning tool 36 is inserted through a second puncture 34' in the eye at the juncture of the cornea and the sclera. The use of a puncture as described hereto is standard operating procedure in cataract surgery and does not require a suture. Puncture 34' is of the order of 1 mm or less, as such incision will accommodate the lateral dimension of the positioning tool 36 which is inserted through puncture 34'. The size of puncture 34' is sufficient to allow tip 48 and part of arm 46 to be inserted therethrough, and accordingly, 1 mm will usually suffice. Tip 48 engages in hole 58 in haptic 56 of lens 50 that is in the eye.

Instead of severing the wrapping of the implant by applying the cutting techniques specifically mentioned in the '393 patent, cutting is effected in accordance with the invention either by laser radiation striking the sheath or wrapping or by an ultrasonic vibratory probe contacting the sheath or wrapping. In either case, the sheath or wrapping is cut and the same procedure as discussed in the '393 patent is followed thereafter. In this application, the words "sheath" and "wrapping" are construed as synonymous. For convenience, "wrapping" will be used henceforth.

The laser radiation is supplied by a Holmium, Erbium, carbon dioxide (if material surrounding the lens had a high water content), diode or YAG laser or any laser with a wavelength suited for cutting purposes. The laser radiation may either be delivered to the wrapping by a contact probe or aimed to strike the wrapping in a non-contact laser delivery system.

The ultrasonic vibratory probe operates in the same manner as the ultrasonic vibratory probes currently in use during cataract surgery to cut tissue. It vibrates at least at ultrasonic speeds; faster speeds may also be used.

The experience of the applicant, who has performed literally thousands of cataract eye operations, has found that during the course of an eye surgical operation, both laser radiation and ultrasonic vibration are effective techniques for cutting tissue. Based on this experience and the applicant's familiarity with wrappings of intraocular lens implants, such techniques are well suited for surgeons who need to cut the wrapping of a rolled intraocular lens.

Once the wrapping is cut and the lens is unrolled, the cut wrapping may be removed in any of the conventional techniques discussed in the '393 patent, e.g., such as with a hooked end of a tool or with standard forceps. Because of the relatively thin and deformable nature of the wrapping, it can be easily removed through the incision.

The '393 patent recommends that a microsurgical positioning tool be inserted through the other incision in the eye to prevent movement of the lens and wrapping within the eye during removal of the small microsurgical instrument that was used to cut the wrapping. Such a positioning tool should also be used in connection with the laser beam and ultrasonic vibratory probe cutting techniques. It prevents the lens and wrapping from moving during removal of the probe that was in contact with the wrapping to effect the cutting.

Of course, if the non-contact laser delivery system is used, the positioning tool is not needed for preventing movement during probe removal because no contact probe is being used. Nevertheless, it may be good practice to use such a positioning tool during removal of the wrapping to keep the lens from moving.

The laser beam and ultrasonic vibratory probe cutting techniques offer some advantages. For instance, no chemical agents need be introduced into the eye for either technique, as would be the case where the wrapping was bonded to itself or to the lens and the bond is chemically dissolved.

In addition, the laser delivery system and the ultrasonic vibration systems may be shut off during insertion and withdrawal of their contact probes with respect to the implant site. Since these probes can not effectively cut tissue while their systems are shut off, they would not create the same risk of severity of injury to the eye upon inadvertent contact with components of the eye during insertion and withdrawal as would be the case for a sharp cutting blade.

As is the case with the cutting techniques discussed in the '393 patent, cutting should be done carefully to avoid damage to the lens implant. Thus, the laser beam should be at a power level and duration of exposure sufficient to cut the wrapping but avoid cutting the underlying lens implant simultaneously and the ultrasonic vibration should be sufficient to cut the wrapping but not cut into the lens implant simultaneously. These laser and ultrasonic vibratory probe cutting techniques offer a more precise method to sever the wrapping, with less chance of damaging the lens implant, than does the mechanical cutting method described in the '399 patent. The use of a magnification aid such as an operating microscope may be useful to see when cutting of the wrapping is complete. At that time, the laser or ultrasonic vibration techniques may be stopped to prevent inadvertent damage to the lens implant or tissue.

FIG. 8 illustrates a first embodiment of the invention in the form of laser apparatus particularly useful for microsurgery. A conventional teaching on the use of laser beam radiation with a YAG laser for cataract surgery is exemplified in U.S. Pat. No. 4,538,608, the contents of which is incorporated hereby by reference.

Figure 3:
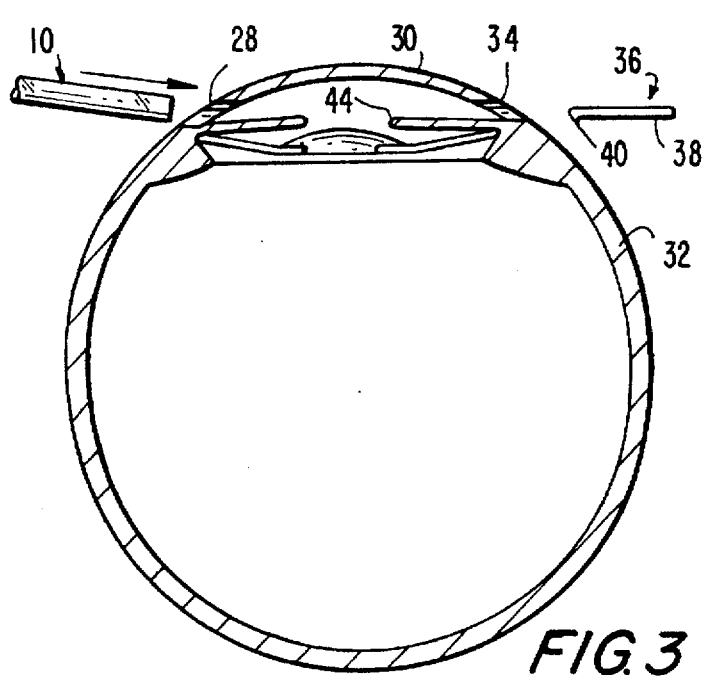
FIG. 3 is a cross-sectional view taken substantially along line 3—3 of FIG. 2.

The laser, generally designated 120 in FIG. 8, outputs a laser beam through a system of articulated arms 122 to a scanner system 124, which directs the beam through to a micro-manipulator 126, such as described in U.S. Pat. No. 4,228,341 whose contents are incorporated herein by reference, to the wrapping to be cut. Micromanipulator 126 includes a joystick 127 enabling the surgeon to manipulate the laser beam as desired, and also an eyepiece and microscope (not shown) to permit the surgeon to view the working area containing the tissue to be cut. The scanner system is effective to scan a continuous laser beam across the wrapping to cut the same. For the sake of convenience, the depiction of the eye corresponds with that of FIG. 3.

The laser beam is directed to strike the wrapping 62 by emerging from an outlet port 128 of the micro-manipulator 126. The laser beam may converge as it travels to and out the outlet port 128. When the cut is complete across the full length of the wrapping along line 64 of FIGS. 6 and 7, the lens unfolds in a conventional manner since it is now free from being held in a wrapped condition. Depending upon the type of laser delivery system used, the outlet port 128 may remain spaced from the wrapping 62 throughout the lasing or be brought into contact with the wrapping 62 perhaps by being part of a movable probe.

Figure 9:
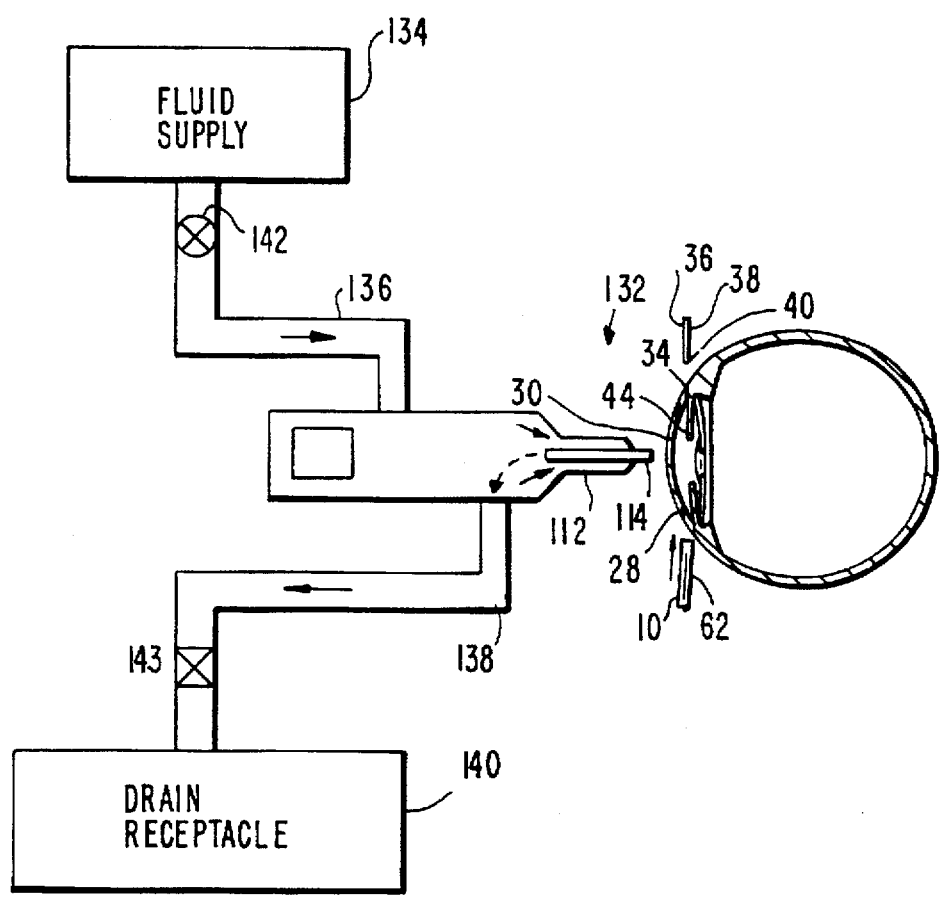
FIG. 9 is a schematic representation of an ultrasonic vibratory system for free-hand surgery in accordance with the invention.

Turning to FIG. 9, an ultrasonic vibratory delivery system in accordance with a second embodiment of the present invention is illustrated. A conventional teaching of the use of an ultrasonic vibratory delivery system to cut tissue in cataract surgery is disclosed, for instance, in issued patents of the applicant, such as U.S. Pat. No. 5,505,693 whose contents of which are incorporated herein by reference.

FIG. 9 shows a system of irrigating fluid into the eye and aspirating fluid and tissue from the eye continuously throughout an eye surgery operation. A conventional phacoemulsification handpiece 132 is shown, which is constructed in any conventional manner. There is a vibratory drive V for vibrating the hollow needle 114. An infusion sleeve 112 is provided that defines a chamber between its inner wall and the outside of the vibrating hollow needle 114. As indicated by the flow arrows, irrigation into the eye is provided normally through this chamber and aspiration from the eye is through the needle 114. The internal construction of the handpiece, such as seals and connecting linkage with the vibratory drive V have been omitted for the sake of brevity and further since such is conventional.

The irrigation is provided from a gravity fed fluid supply 134 and through an infusion tube 136 to the handpiece 132. Aspiration is provided through a discharge tube 138 from the handpiece 132 to a drain receptacle 140. In a known manner, a gate valve 142 is provided to permit flow through the infusion tube to occur. The fluid supply 134 is at a higher elevation than the eye. A pumping mechanism 143 is present and, when activated, suctions fluid from the eye and through discharge tube 138.

The vibratory drive V is actuated to drive the needle 114 into vibratory contact with the wrapping 62 of the implant, thereby cutting the same in the same manner that tissue is cut during cataract surgery. The needle is moved along a widthwise direction of the rolled implant, that is, transverse to the direction in which the wrapper wraps. Once the cutting is complete along the full width of the wrapping, the lens unfolds in a conventional manner because it is now free from being held in the wrapped condition.

In both the embodiments of FIGS. 8 and 9, the cutting takes place preferably in a widthwise direction of the wrapping 62, i.e., transverse to the direction in which the wrapping is rolled into the rolled condition.

Since the cutting of the wrapping does not require that the wrapping be broken up into bits, the needle 114 need not be hollow to suction out the wrapping and the eye does not need to be irrigated during the cutting of the wrapping. Thus, the needle 114 need not be hollow and may be solid. However, for convenience, the same phacoemulsification handpiece used to cut tissue during cataract surgery may be used to cut the wrapping in the widthwise direction.

While the foregoing description and drawings represent the preferred embodiments of the present invention, it will be understood that various changes and modifications may be made without departing from the spirit and scope of the present invention.

What is claimed is:

1. A method of removing a wrapping from an intraocular lens within an eye, comprising the steps of:

aiming a laser beam at a wrapping that wraps at least a portion of an intraocular lens, the lens being in a rolled condition within the eye and the wrapping being pliable;

cutting the wrapping with the laser beam until the lens is free to unroll within the eye; and removing the cut wrapping from the eye.

2. A method as in claim 1, further comprising the step of generating the laser beam with a laser, wherein the laser beam has a wavelength suited for cutting the wrapping.

3. A method as in claim 1, further comprising the step of moving an outlet port into contact with the wrapping, the step of cutting including delivering the laser beam to the wrapping through the port.

4. A method as in claim 1, wherein the step of cutting includes delivering the laser beam to the wrapping through an outlet port, the port being spaced from and out of contact with the wrapping.

5. A method as in claim 1, wherein the wrapping has a widthwise direction that is transverse to the direction in which the wrapping is rolled in the rolled condition, the step of cutting taking place across a full width of the wrapping in the widthwise direction.

6. A method of removing a wrapping from an intraocular lens within an eye, comprising the steps of:

directing an ultrasonic vibratory probe into contact with a wrapping that wraps at least a portion of an intraocular lens, the lens being in a rolled condition within the eye and the wrapping being pliable;

actuating the probe to vibrate at a speed sufficient to cut the wrapping;

cutting the wrapping with the actuating probe until the lens is free to unroll within the eye; and removing the cut wrapping from the eye.

7. A method as in claim 6, wherein the wrapping has a widthwise direction that is transverse to the direction in which the wrapping is rolled in the rolled condition, the step of cutting taking place across a full width of the wrapping in the widthwise direction.

8. A method as in claim 6, wherein the ultrasonic vibratory probe is actuated as part of a phacoemulsification handpiece.

9. A method as in claim 6, wherein a cutting portion of the actuating probe is vibrating at least at ultrasonic speeds.

\* \* \* \* \*